United States Patent
Kargman et al.

(10) Patent No.: US 6,649,649 B1
(45) Date of Patent: Nov. 18, 2003

(54) METHOD OF TREATING COLONIC ADENOMAS

(75) Inventors: Stacia Kargman, Hampstead (CA); Thomas J. Simon, Berwyn, PA (US); Jilly Evans, Brossard (CA)

(73) Assignees: Merck & Co., Inc., Rahway, NJ (US); Merck Frosst Canada, & Co., Kirkland (CA)

( * ) Notice: Subject to any disclaimer, the term of this patent is extended or adjusted under 35 U.S.C. 154(b) by 0 days.

(21) Appl. No.: 09/261,034

(22) Filed: Mar. 2, 1999

Related U.S. Application Data (62) Division of application No. 08/948,873, filed on Oct. 10, 1997, now Pat. No. 5,968,974, which is a continuation of application No. 08/683,290, filed on Jul. 18, 1996, now abandoned.
(60) Provisional application No. 60/001,240, filed on Jul. 19, 1995.

(51) Int. Cl.$^7$ ............................................. A61K 31/34
(52) U.S. Cl. .............. 514/461; 514/241; 514/242; 514/252; 514/267; 514/359; 514/363; 514/365; 514/372; 514/374; 514/378; 514/383; 514/451; 514/444; 514/473; 514/499
(58) Field of Search ........................ 514/241, 242, 514/252, 267, 359, 363, 365, 372, 374, 378, 383, 451, 444, 473, 499, 461

(56) References Cited

U.S. PATENT DOCUMENTS

| | | | |
|---|---|---|---|
| 4,267,184 A | 5/1981 | Cherkofsky | |
| 5,135,940 A | 8/1992 | Belanger et al. | 514/381 |
| 5,474,995 A | 12/1995 | Ducharme et al. | 514/241 |
| 5,604,260 A | * 2/1997 | Guay et al. | 514/605 |
| 5,616,601 A | * 4/1997 | Khanna | 514/399 |
| 5,633,272 A | * 5/1997 | Talley | 514/378 |
| 5,968,974 A | 10/1999 | Kargman et al. | |

FOREIGN PATENT DOCUMENTS

| | | |
|---|---|---|
| WO | WO 9415932 | 7/1994 |
| WO | WO 94/27980 | 12/1994 |
| WO | WO 95/00501 | 1/1995 |
| WO | WO 95/15316 | 6/1995 |
| WO | WO 95/15318 | 6/1995 |
| WO | WO 95/18799 | 7/1995 |
| WO | WO 96/03392 | 2/1996 |
| WO | WO 96/10105 | 4/1996 |
| WO | WO 96/10106 | 4/1996 |
| WO | WO 96/19469 | 6/1996 |
| WO | WO 96/36617 | 11/1996 |
| WO | WO 96/41645 | 12/1996 |

OTHER PUBLICATIONS

Ninomiya et al. "Experimental studies on antitumor . . . " CA 108:197985, 1987.*
Choi et al. "The effect of colostomy . . . " CA 115:117124, 1990.*
Tanaka et al. "Inhibitory effect of the non–steroidal . . . " CA 115:270156, 1991.*
O'Neil et al. "Selective inhibitors of cox–2" CA 123:101767, 1995.*
Greenberg et al. "Aspirin and . . . " CA 126:228, 1996.*
Dubois et al. "Cyclooxygenase . . . " CA 126:98753, 1996.*
Tanaka et al. "Chemoprevention of . . . " CA 127:44539, 1997.*
Murphy et al. "Cyclooxygenase–2 . . . " CA 128:188436, 1998.*
Nichtberger et al. "Combination therapy . . . " CA 131:209130, 1998.*
Ponz et al. "Evidence for the existence of . . . " Medline 90258505, 1990.*
Kurumbail et al. "Structural basis for selective . . . "Nature v.384, 644–648, 1996.*
Isakson, CA 126:166480 (1996).
Isakson, CA 126:166479 (1996).
Talley, CA 126:74828 (1996).
Bertenshaw, CA 121:179484 (1994).
Norman, CA 122:314540 (1994).
Herman, CA 111:111037 (1989).
Cherkofsky, CA 95:61982 (1981).
Dubois, R.N., Medline Abstracts, No. 95212855, Gastroenterology, vol. 108 (4), pp. 1310–1314, (1995).
Sano, et al., Medline Abstracts No. 95368634, Cancer REsearch, vol. 55 (17), pp. 3785–3789, (1995).
Marnett, L.J. Abstract No. 93–02144, Cancer Res., vol. 55 (2), pp. 55k75–5589, (1992).
Narisawa, et al., Medline abstract No. 88007002m, Japan J. Cancer Res., vol. 78 (8), pp. 791–198, (1987).
Narisawa, et al. Medline Abstract No. 86267824, Japan J. Cancer & Chem., vol. 13 (4Pt. 2), pp. 1329–1335, (1986).
E. Wong, et al., Inflam. Res. 46: 51–59 (1997).
D. Riendeau, et al. Brit J. Pharmacol. 121: 105–117 (1997).
O.H. Callan, et. al., J. Biol Chem. 21 (7): 2548–3554 (1996).
S. Kargman, et al., Biochem. Pharmacol. 52: 1113–1125 (1996).
M. Ouellet, et al. Biochem. J. 306: 247–251 (1995).
Giardello, F. Cancer and Metastasis Rev. 13: 279–283(1994).

(List continued on next page.)

*Primary Examiner*—Ceila Chang
(74) *Attorney, Agent, or Firm*—Raynard Yuro; Richard C. Billups; David L. Rose (57) ABSTRACT

This invention is directed to a method of retarding or preventing the transformation of a colonic adenoma to a colonic adenocarcinoma comprising the administration to a patient with FAP or a patient with one or more of said adenomas a non-toxic therapeutically effective amount of NSAID, said amount effective to inhibit the PGHS-2 in said adenoma. The preferred method comprises the administration of a specific PGHS-2 inhibiting agent as defined herein.

19 Claims, 3 Drawing Sheets

OTHER PUBLICATIONS

O'Neill, G. , et. al., Molec, Pharmacol. 45: 245–254 (1993).
B.S. Reddy, et al., Cancer Res. 50: 2562–2568 (1990).
Kargman, S.L., et al., Cancer Research, vol. 55, pp. 2556–2559, 1995.
Oshima, M., et al., Cell, pp. 803–809, 1996.
Isakson, CA 126:166481 (1996).
Tanaka et al. "Inhibitory effecto of the nonsteroidal antiinflammatory drug indomethacin on the naturally occurring carcinogen 1–hydroxyanthrazuinone in male ACI/N rats" Carcinogenesis v.12 pp. 1949–1952 (1991).*
Rao et al. "Chemoprevention of colon carcinogenesis by sulindac a nonsteroidal antiinflammatory agent" Can. Res. v.55, pp. 1464–1472 (1995).*
Grossman et al. "Inhibition of constitutive and inducible cyclooxygenase activity in human platelets and mononuclear cells by NSAIDS and Cox2 inhibitors" Inglamm. Res. v. 44 pp. 253–257 (1995).*
Taketo "Cyclooxygenase–2 inhibitors in tumorigenesis" J. Nat. Can. Inst. v. 90, pp. 1529–1536 (1998).*
Willoughby et al. "COX–1, COX–2, and COX–3 and the future treatment . . . " CA 133:87359 (2000).*
D. Reindieu et al., Canadian Journal of Physiology and Pharmacology, vol. 75, pp. 1088–1095. 1997.
T. Warner et al., Proc. Natl. Acad. Sci. USA, vol. 96, pp. 7563–7568. 1999.
L. Sheehan et al., Journal of the American Medical Association, vol. 282, No. 13, pp. 1254—1257. 1999.
C. Chan et al., J. Pharmacol. Exp. Ther., vol. 274, pp. 1531–1537. 1995.
B. Battistini, et al., Drug News Perspectives, vol. 7, pp. 501–512. 1994.
C. Torrance et al., Nature Medicine, vol. 6, No. 8. 2000.
E. Wong et al., J. Biological Chemistry, vol. 272, No. 14, pp. 9280–9286, 1997.
W. Cromlish, et al., Biochemical Pharmacology, vol. 52, pp. 1777–1785. 1996.
T. Penning et al., J. Med. Chem., vol. 40, pp. 1347–1365. 1997.
R. Copeland et al., Med. Chem. Res., vol. 5, pp. 384–393. 1993.
R. Copeland et al., Proc. Natl. Acad. Sci. USA, vol. 91, pp. 11202–11206. 1994.
J. Gierse, et al., Biochem. J., vol. 339, pp. 607–614. 1999.
J. Gierse, et al., Biochem, J., vol. 305, pp. 479–484. 1995.
R. Jacoby, Cancer Research, vol. 60, pp. 5040–5044. 2000.
J. Masferrer, Cancer Research, vol. 601–pp. 1306–1311. 2000.
B. Reddy, Cancer Research, vol. 60, pp. 293–297. 2000.
B. Reddy, Cancer Research, vol. 56, pp. 4566–4569. 1996.
T. Kawamori, Cancer Research, vol. 58, pp. 409–412, 1998.
Huang et al., Exp. Opin. Invest. Drugs, vol. 4, No. 3, pp. 243–249. 1995.
C. Papparlardo, Surg. Res. Comm., vol. 14, pp. 97–102, 1993.
M. Ponz De Leon, J. of Surgical Oncology, vol. 44, pp. 35–43. 1990.
R. DuBois, J. Gastroenterol., vol. 31, No. 6, pp. 898–906. 1996.
P. Patrignani et al., J. Pharmacol. Exp. Ther., vol. 271, pp. 1705–1712. 1994.
L. J. Marnett, Preventive Medicine, vol. 24, No. 2, pp. 103–106. 1995.
R. N. DuBois, Medline Abstracts No. 95212855, Gastroenterology, vol. 108, No. 4, pp. 1310–1312. 1995.
Eberhart, et al., Gastroenterology, vol. 107, pp. 1183–1188. 1994.
Giardiello, N. Eng. J. Med., vol. 328, pp. 1313–1116. 1993.
E. Giovanucci, et al., Annals of Internal Medicine, vol. 121, No. 4, pp. 241–246. 1994.
Herschman, Can. Mer. Rev., vol. 113, pp. 241–256. 1994.
Meade, et al., Jornal of Biological Chemistry, vol. 268, pp. 6610–6614. 1993.
Brideau, et la., Inflamm. Res., vol. 45, pp. 68–74. 1996.
Cryer, et al., Am. J. Med., vol. 104, pp. 413–421. 1998.
Giulano et al., Brit. J. Pharmacol., vol. 126, pp. 1824–1830. 1999.
Laneauville, et al., J. of Pharmacology and Experimental Therapeutics, vol. 271, pp. 927–934. 1994.
D. L. DeWitt, et al., Am. J. Med. (Suppl.), vol. 95, pp. 405–445. 1993.
L. Hixon, et al., Cancer Epidemiology, Biomarkers and Prevention, American Association for Cancer Research, vol. 3, No. 5, pp. 433–438. 1994.
Ricketts et al. "Evaluation of selective inhibition of canine cyclooxygenase . . . " CA130:162885 (1998).*
Blanco et al. "Effect of antiinflammatory drugs on COX1 . . . " CA 131:193940 (1999).*
Dannhardt et al. "In vitro test system . . . " CA 135282613 (2001).*
Tegeder et al. "Effects of selective COX–1 and – 2 inhibition . . . " CA 136:145141 (2001).*
Francis M. Giardiello, et al., "Primary Chemoprevention of Familial Adenomatous Polyposis with Sulindac", The New England Journal of Medicine, *346*(14):1054–1059 (2002).
G. Steinbach, et al, "TheEffect of Celecoxib, A Cyclooxygenase–2 Inhibitor, In Familial Adenomatous Polyposis", The New England Journal of Medicine, *342*(26):1946–1952 (2000).
Logan, R. F. A., et al., Gastroenterology, vol. 106, No. 4, p. A409, 1994.
Metzcer, U. et al., Diseases of the Colon and Rectum, vol. 27, No. 6, pp. 366–369, 1984.
Arvind, Padma, et al. Biochemistry, vol. 34, No. 16, pp. 5604–5609, 1995.
Barnes, C. J. et al., Cell Proliferation, vol. 28, No. 2, pp. 59–71, 1995.
Giovannucci, Edward, et al. Annals of Internal Medicine, Bol. 1221, No. 4, pp. 241–246. 1994.
Muller, Astrid, D., et al.; Digestive Diseases and Sciences, vol. 39, No. 11, pp. 2480–2484.1994.
Heath Clark, W. Jr., et al., Cancer, vol. 74, No. 10, pp. 2885–2888, 1994.
Reddy, Bandaru, S., et al. Carcinogenesis, vol. 14 (8), pp. 1493–1497, 1993.
Yoshikawa, Reigetsu, et al.Oncol. Rep., vol. 2 (3), pp. 361–364 1995.
Muscat, Joshua, et al., Cancer, EPO vol. 74, No. 7, pp. 1874–1854, 1994.
Davis, A. et al., Australian and new Zealand Journal of Medicine, vol. 24, No. 3, pp. 301–303, 1994.
Trujillo. M. Angelo et al., Digestive Diseases and Sciences, vol. 39, No. 10, pp. 2260–226, 1994.
Wargovich, Michael J., et al. International Journal of Cancer, vol. 60 No. 4, pp. 515–519, 1995.
Steel, G. Jr, et al. Currrent Problems in cancer, vol. 17 (4), pp. 223–269, 1993.
Karen Muller–Decker, et al., Molecular Carcinogensis, vol. 12, pp. 31–41, 1995.

* cited by examiner

METHOD OF TREATING COLONIC ADENOMAS

CROSS REFERENCE TO RELATED APPLICATIONS

This application is a divisional application of U.S. application Ser. No. 08/948,873 filed on Oct. 10, 1997, now U.S. Pat. No. 5,968,974 granted on Oct. 19, 1999, which was a continuation of U.S. application Ser. No. 08/683,290 filed on Jul. 18, 1996, now abandoned, which was based upon provisional application No. 60/001,240 filed on Jul. 19, 1995, now lapsed, priority of which is claimed hereunder.

BACKGROUND OF THE INVENTION

This application is directed to a method of treating colonic adenomas by administration of a non-toxic therapeutically effective amount of an non-steroidal anti-inflammatory agent (NSAID). In particular, this application is directed to a method of preventing or retarding the transformation of colonic adenomas to colonic adenocarcinomas by administration of a non-toxic therapeutically effective, specific PGHS-2 inhibitor.

The enzyme prostaglandin G/H synthase (PGHS) is a key enzyme in the biosynthetic pathway leading to the formation of prostaglandins (Watkins, W. D., Peterson, M. B., and Fletcher, J. R. ed. Prostaglandins in Clinical Practice. New York: Raven, 1989 and Dewitt, D'. L. Prostaglandin endoperoxide synthase: regulation and enzyme expression. Biochim. Biophys. Acta, 1083; 121–134, 1991). These prostanoids are potent biological mediators with diverse normal physiological effects and are also implicated in a variety of pathological conditions including inflammation and neoplastic transformation (Watkins, W. D., Peterson, M. B., and Fletcher, J. R. ed. Prostaglandins in Clinical Practice. New York: Raven, 1989 and Dewitt, D. L. Prostaglandin endoperoxide synthase: regulation and enzyme expression. Biochim. Biophys. Acta, 1083; 121–134, 1991 and Xie, W., Robertson, D. L., and Simmons, D. L. Mitogen-inducible prostaglandin G/H synthase: a new target for nonsteroidal anti-inflammatory drugs. Drug Dev. Res., 25; 249–265, 1992). Two isoforms of PGHS have been identified (Loll, P. J. and Garavito, R. M. The isoforms of cyclooxygenase: structure and function. Expert Opin. Invest. Drugs, 3; 1171–1180, 1994). PGHS-1 is constitutively expressed in most tissues and has been proposed to generate prostaglandins for normal physiological functions. The second isoform, PGHS-2, is characterized by a rapid induction by a variety of stimuli, including mitogens, hormones, cytokines and growth factors (Loll, P. J. and Garavito, R. M. The isoforms of cyclooxygenase: structure and function. Expert Opin. Invest. Drugs, 3; 1171–1180, 1994 and Battistini, B., Botting, R., and Bakhle, Y. S. COX-1 and COX-2: Toward the development of more selective NSAIDS. Drug News Perspectives, 7; 501–512, 1994). In conditions such as inflammation, PGHS-2-derived prostaglandins may be the predominant effectors (Masferrer, J. L., Zweifel, B. S., Manning, P. T., Hauser, S. D., Leahy, K. M., Smith, W. G., Isakson, P. C., and Seibert, K. Selective inhibition of inducible cyclooxygenase 2 in vivo is anti-inflammatory and non-ulcerogenic. Proc. Natl. Acad. Sci. USA, 91; 3228–3232, 1994). Both PGHS-1 and PGHS-2 have been shown to be the target of nonsteroidal anti-inflammatory drugs (NSAIDs) (Battistini, B., Botting, R., and Bakhle, Y. S. COX-1 and COX-2: Toward the development of more selective NSAIDS. Drug News Perspectives, 7; 501–512, 1994 and O'Neill, G. P., Mancini, J. A., Kargman, S., Yergey, J., Kwan, M. Y., Falgueyret, J. -P., Abramovitz, M., Kennedy, B. P., Ouellet, M., Cromlish, W., Culp, S., Evans, J. F., Ford-Hutchinson, A. W. and Vickers, P. J. Overexpression of human prostaglandin G/H synthase-1 and -2 by recombinant vaccinia virus: inhibition by nonsteroidal anti-inflammatory drugs and biosynthesis of 15-hydroxyeicosatetraenoic acid. Mol. Pharmacol., 45; 245–254, 1994 and DeWitt, D. L., Meade, E. A., and Smith, W. L. PGH synthase isoenzyme selectivity: the potential for safer nonsteroidal anti-inflammatory drugs. Am. J. Med. (Suppl.), 95; 40S–44S, 1993). See also WO 94/14977, published Jul. 7, 1994, which discloses a method of evaluating the potency of PGHS-2 inhibiting agents as well as the selectivity for PGHS-2 over PGHS-1.

Elevated levels of prostaglandins have been demonstrated in various cancers including lung and colon carcinomas (McLemore, T. L., Hubbard, W. C., Litterst, C. L., Liu, M. C., Miller, S., McMahon, N. A., Eggleston, J. C., and Boyd, M. R. Profiles of prostaglandin biosynthesis in normal lung and tumor tissue from lung cancer patients. Cancer Res., 48; 3140–3147, 1988 and Rigas, B., Goldman, I. S., and Levine, L. Altered eicosanoid levels in human colon cancer. J. Lab. Clin. Med., 122; 518–523, 1993). In particular, prostaglandin levels have been shown to be elevated in benign adenomatous polyps and further increased in cancerous colon tissue, as compared to histologically normal mucosa. Since prostanoids have been shown to be immunosuppressive, they may play a role in tumor development (Earnest, D. L., Hixson, L. J., and Alberts, D. S. Piroxicam and other cyclooxygenase inhibitors: potential for cancer chemoprevention. J. Cell. Biochem., 161 (Suppl.); 156–166, 1992).

Since the late 1970's, investigators have considered the possibility that aspirin and related nonsteroidal anti-inflammatory drugs (NSAIDs) might be beneficial to the treatment of certain cancers, including colon cancer.

The first epidemiological study suggesting that aspirin might reduce the risk of colorectal cancer came in 1988 in a retrospective, exploratory analysis from Melbourn, Australia (Cancer, Res., 48: 4399–4404, 1988). The study found a 40 percent lower risk of incident colon cancer among persons who regularly used aspirin compared to those who used no aspirin. More recently the data of Heath, et al, suggests the possible benefit of NSAIDs for prevention of colorectal neoplasms (Heath, C. W., Jr., Thun, M. J., Greenberg, E. R., Levin, B., and Marnett, L. J. Nonsteroidal anti-inflammatory drugs and human cancer. Cancer, 74; 2885–2888, 1994). However, despite this and subsequent studies, there has been no hard evidence linking the use of and the prevention of colon cancer, nor has there been any hard evidence demonstrating a pathological link between colorectal cancer and PGHS or the therapeutic value of inhibiting PGHS by administration of aspirin. For example, arthritis patients (many of whom take aspirin) may simply be less prone to cancer of the colon.

In this application we disclose studies in which we have analyzed the expression of human PGHS-1 and PGHS-2 protein in 25 paired normal and autologous colon tumors, 4 premalignant colon polyps, 5 control colon tissues (from non-cancer patients) and 3 matched normal and cancerous human breast tissues. Among the observations from this study are that PGHS-1 protein is reduced in colon tumor tissue as compared to histologically normal colonic mucosa, and that PGHS-2 is detected in the majority of colon tumor samples while being virtually undetectable in normal tissues, polyps and breast cancer samples. The increased levels of prostaglandins in tumor tissue of the colon is derived from the inducible PGHS-2 isoform. These studies support our belief that the transformation of a colonic adenoma to a colonic adenocarcinoma is mediated by the dramatic and surprising over production of PGHS-2 in the adenoma. Accordingly, we have surprisingly found a method of retarding or preventing the transformation of a colonic adenoma to an colonic adenicarcinoma comprising the administration to a patient with a history of FAP (Familial adenomatous Polyposis) or a patient with one or more colonic adenomas a non-toxic therapeutically effective amount of NSAID; said amount effective to inhibit the PGHS-2 in said adenoma.

SUMMARY OF THE INVENTION

This invention is directed to a method of retarding or preventing the transformation of a colonic adenoma to a colonic adenocarcinoma comprising the administration to a patient with FAP or a patient with one or more of said adenomas a non-toxic therapeutically effective amount of NSAID, said amount effective to inhibit the PGHS-2 in said adenoma. The preferred method comprises the administration of a specific PGHS-2 inhibiting agent as defined herein.

DETAILED DESCRIPTION OF THE FIGURES

Figure 1A:
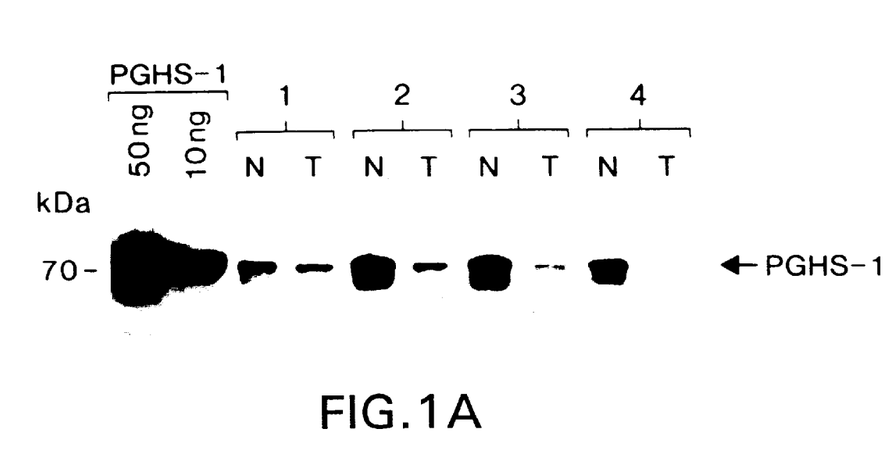
FIG. 1 Representative immunoblot analysis of PGHS-1 and PGHS-2 protein expression in normal human colonic mucosa and autologous tumor tissue.
Figure 1B:
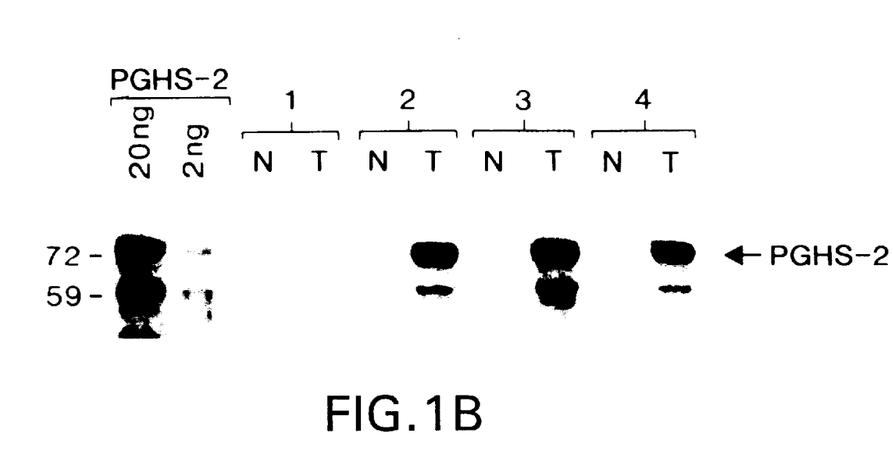

FIG. 1. Representative immunoblot analysis of PGHS-1 and PGHS-2 protein expression in normal human colonic mucosa and autologous tumor tissue. Immunoblot analysis using an anti-PGHS-1 antiserum (panel A) and immunoblot analysis of the same samples as those shown in panel A using anti-PGHS-2 antiserum (panel B). Purified PGHS standards and microsomal protein samples (50 µg per lane) were separated by SDS-PAGE, transferred to nitrocellulose, and immunoblotted with anti-PGHS antisera with detection by enhanced chemiluminescence. Numbers 1–4 indicate samples from 4 representative patients of 25 patients examined. The densitometric values for patients 1–4 in this figure correspond to patients 17–20 shown in FIG. 2. N and T denote matched normal colonic mucosa and tumor tissue for each patient, respectively. Purified PGHS-1 and PGHS-2 standards are shown at the left. The positions of molecular weight markers are indicated.

Figure 2:
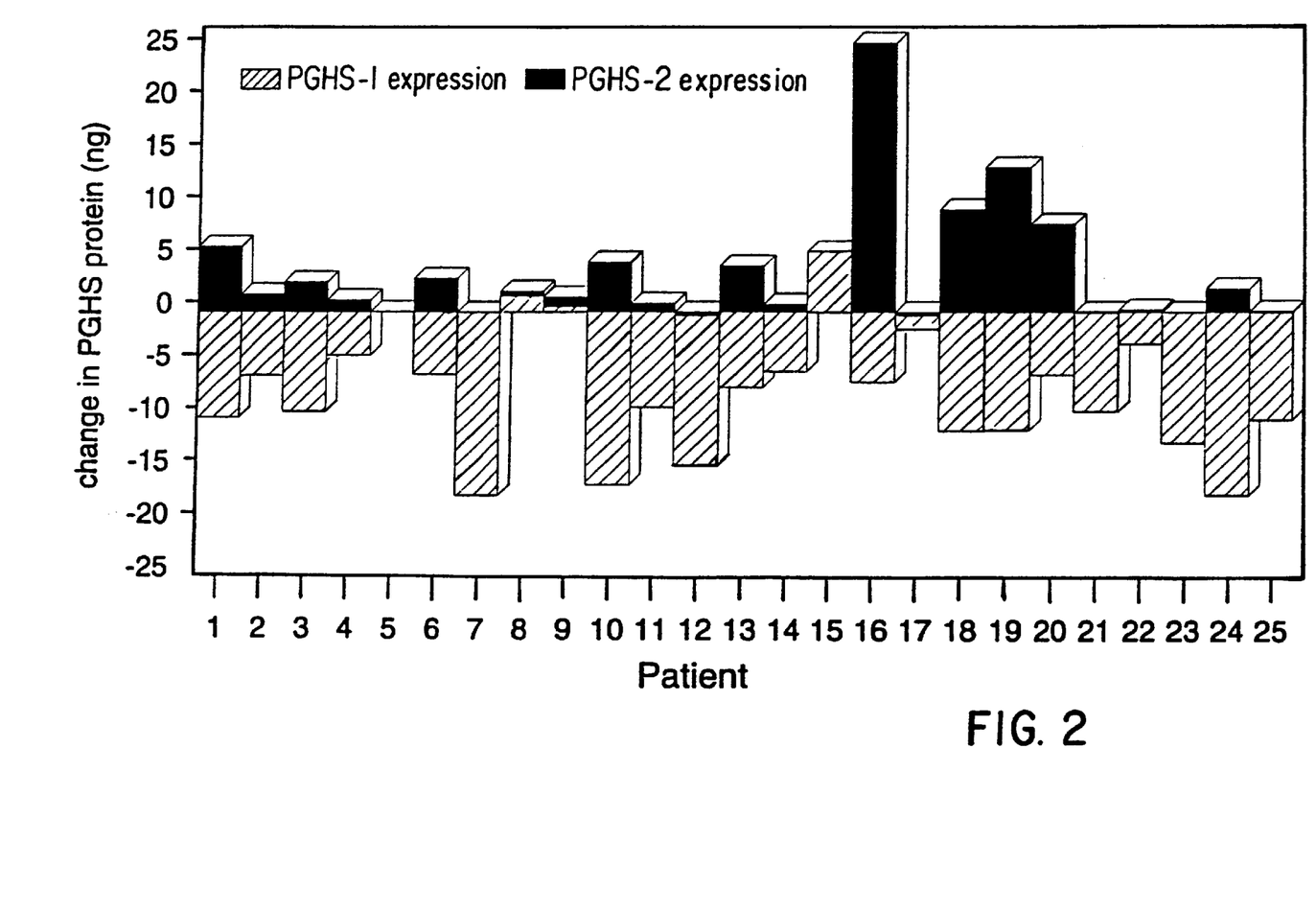
FIG. 2 Quantitation of change in PGHS-1 and PGHS-2 protein expression in matched tumor as compared to autologous normal mucosa.

FIG. 2. Quantitation of change in PGHS-1 and PGHS-2 protein expression in matched tumor tissue as compared to autologous normal mucosa. Aliquots of PGHS standards and of microsomal proteins from 25 patients (50 µg per lane) were separated by SDS-PAGE, transferred to nitrocellulose, and immunoblotted with anti-PGHS-1 or anti-PGHS-2 antisera, with detection by enhanced chemiluminescence. The amounts of PGHS protein were determined by densitometry. The optical density reading from the scanned autoradiograph for known quantities of purified PGHS-1 and PGHS-2 standards were used to quantitate approximate amounts of PGHS-1 and PGHS-2 protein in microsomal samples from normal mucosa and tumor samples. Values represent the change in expression in ng from normal mucosa to tumor tissue for each patient.

Figure 3:
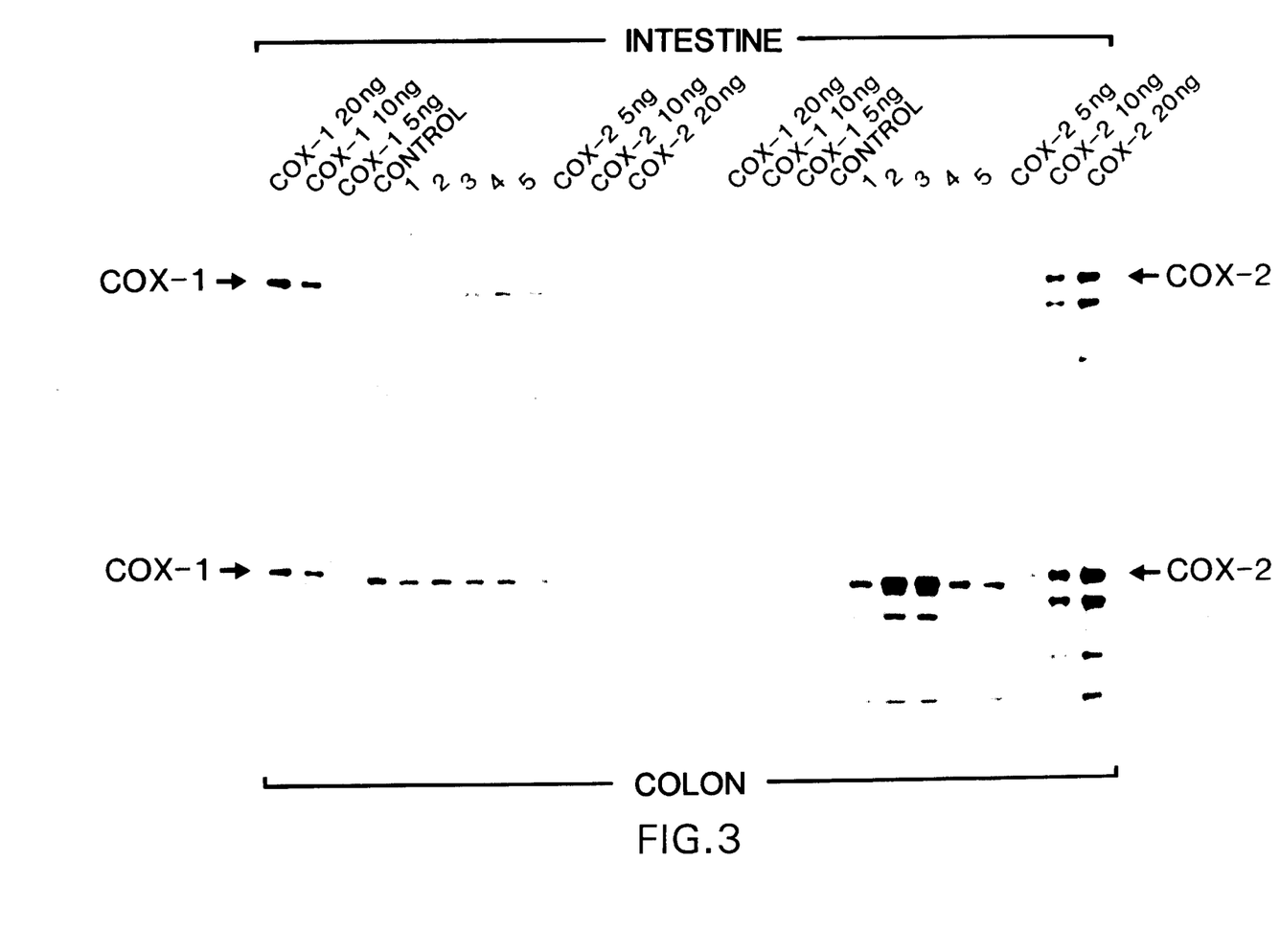
FIG. 3 Immunoblot analyses demonstrating PGHS-1 and PGHS-2 expression in polyps in ApcΔ716 knockout mice ranging in size from 0.3–5 mm in diameter.

FIG. 3 An immunoblot analyses demonstrating PGHS-1 and PGHS-2 expression in polyps ranging in size from 0.3–5 mm in diameter. (Lanes 1–5 correspond to samples derived from polyps of approximately 1–5 mm in diameter, respectively.) PGHS-1 protein was demonstrated in all intestinal and colonic control and polyps samples. PGHS-2 immunoreactivity was not detected in control intestine or colon samples. Although low levels of PGHS-2 protein were detected in larger intestinal polyps (3–5 mm in diameter) (lanes 3,4 and 5), higher levels of PGHS-2 immunoreactive species were detected in all colonic polyp samples ranging in size from 1–5 mm in diameter (lanes 1–5) with very high levels of PGHS-2 protein being demonstrated in polyps of 2–3 mm in diameter (lanes 2 and 3). Purified sheep PGHS-1 and PGHS-2 protein (5 ng, 10 ng, and 20 ng) were electrophoresed as standards and are labeled accordingly.

DETAILED DESCRIPTION OF THE INVENTION

In one embodiment this invention is directed to a method of retarding or preventing the transformation of a colonic adenoma to a colonic adenocarcinoma comprising the administration to a patient with a history of FAP or patients with one or more adenomas a non-toxic therapeutically effective amount of NSAID, said amount effective to inhibit PGHS-2 in said adenoma.

For purposes of this specification, such NSAIDs includes, but is not limited to aspirin, ibuprofen, INDOMETHACIN, SULINDAC, DOLOBID, DICLOFENAC, NAPROXEN, PIROXICAN, ETODOLAC, KETOPROFEN, FLURBIPROFEN, MELOXICAM, FLOSULIDE and NABUMETONE.

As is appreciated by those of skill in the art, a milestone event in the transformation of a colonic adenoma to a colonic adenocarcenoma is the acquired capacity of ademona cells to invade the basement membrane of the submucousal tissue of the colon.

Accordingly, within this embodiment is a genus of invention directed to a method of retarding or preventing the appearance of the capacity of a ademona or a cellular portion thereof to invade the basement membrane of the submucousal tissue of the colon comprising the administration to a patient with a history of FAP or patients with one or more adenomas a non-toxic therapeutically effective amount of NSAID, said amount effective to inhibit PGHS-2 in said adenoma.

In one genus of this embodiment, this invention is directed to the use of NSAID's which are potent PGHS-2 inhibiting agents. For purposes of this specification an NSAID is potent if it possess an $IC_{50}$ for the inhibition of PGHS-2 of 1 µM or less as measured by the cell or microsomal assay disclosed herein.

In one subgenus of this genus the invention is directed to the use of NSAIDS which are specific inhibitors of PGHS-2. For purposes of this specification NSAIDS which are specific inhibitors of PGHS-2 is defined as those which possess a specificity for inhibiting PGHS-2 over PGHS-1 of at least 100 fold as measured by the ratio of $IC_{50}$ for PGHS-2 over $IC_{50}$ for PGHS-1 evaluated by the cell or microsomal assay disclosed hereinunder. Such compounds include, but are not limited to those disclosed in WO 94/13635, published Jun. 3, 1994, WO 95/00501, published Jan. 5, 1995, WO 94/15932, published Jul. 21, 1994, U.S. Pat. No. 5,344,991, issued Jun. 6, 1994, EP 0 418 845, published Mar. 27, 1991, U.S. Pat. No. 5,380,738, issued Jan. 10, 1995, and U.S. Pat. No. 5,393,790, issued Feb. 20, 1995, all of which are hereby incorporated by reference.

The ability of the compounds to inhibit PGHS-1 and PGHS-2 can be determined by measuring the activity of the compounds for PGHS-1 and PGHS-2 in the CHAPS-solubilized recombinant PGHS-1 or PGHS-2 expressing insect cell membrane assay as follows:

a. Preparation of recombinant PGHS baculoviruses

A 2.0 kb fragment containing the coding region of either human or murine PGHS-1 or human or murine PGHS-2 is cloned into a BamH1 site of the baculovirus transfer vector pVL1393 to generate the baculovirus transfer vector. Recombinant baculoviruses are isolated by transfecting 4 µg of baculovirus transfer vector DNA into SF9 cells (210e8) along with 200 ng of linearized bacium phosphate method. Recombinant viruses are purified by three rounds of plaque purification and high titer (10E7–10E8 pfu/ml) stocks of virus are prepared. For large scale production, SF9 insect cells are infected in 10 liter fermentors ($0.5 \times 10^6$/ml) with the recombinant baculovirus stock such that the multiplicity of infection is 0.1. After 72 hours the cells are centrifuged and the cell pellet homogenized in Tris/Sucrose (50 mM: 25%, pH 8.0) containing 1% CHAPS. The homogenate are centrifuged at 10,000×G for 30 minutes, and the resultant supernatant stored at −80° C. before being assayed for PGHS activity.

b. Assay for PGHS-1 and PGHS-2 activity:

PGHS activity is assayed as $PGE_2$ formed/µg protein/time using an ELISA to detect the prostaglandin released. CHAPS-solubilized insect cell membranes containing the appropriate PGHS enzyme are incubated in a potassium phosphate buffer (50 mM, pH 8.0) containing epinephrine, phenol, and heme with the addition of arachidonic acid (10 µM). Compounds are pre-incubated with the enzyme for 10–20 minutes prior to the addition of arachidonic acid. Any reaction between the arachidonic acid and the enzyme is stopped after ten minutes at 37° C./room temperature by transferring 40 µl of reaction mix into 160 µl ELISA buffer and 25 µl indomethacin. The $PGE_2$ formed is measured by standard ELISA technology (Cayman Chemical).

This invention is directed to a method of retarding or preventing the transformation of an adenoma to an adenocarcinoma comprising the administration to a patient with one or more adenomas a non-toxic therapeutically effective amount of NSAID, said amount effective to inhibit the production of PGHS-2 in said adenoma. The preferred method comprises the administration of a specific PGHS-2 inhibiting agent as defined herein.

In a second genus the invention is directed to a method of retarding or preventing the transformation of an adenoma to an adenecarcinoma comprising the administration to a patient with one or more adenomas a non-toxic therapeutically effective amount of compound of formula I

I wherein A, B and C are each independently selected from the group consisting of (a) hydrogen, (b) F, Cl, Br or I, (c) methyl or ethyl, (d) $CF_3$, (e) vinyl, (f) $OCH_3$ or $OCF_3$, (g) $SCH_3$ or $SCF_3$, (h) CN, (i) $N_3$, with the proviso that at least one of A, B and C must be hydrogen.

Within genus there is a sub-genus directed to the use of compounds of formula I wherein A and B are each independently selected from the group consisting of (a) hydrogen, (b) F, Cl, Br or I, (c) methyl or ethyl, (d) $CF_3$, (e) vinyl,

(g) $SCH_3$ or $SCF_3$, (h) CN, (i) $N_3$, and C is hydrogen.

Within the class is the sub-class directed to the use of compounds of the formula wherein B is (a) hydrogen, (b) F, Cl, Br or I, (c) methyl or ethyl,

(d) $CF_3$,

(e) vinyl, (f) —$OCF_3$, or (g) —$SCH_3$.

Illustrating this aspect of the invention is the use of a compound selected from or a pharmaceutically acceptable salt thereof.

In a third genus the invention is directed to a method of retarding or preventing the transformation of an adenoma to an adenecarcinoma comprising the administration to a patient with one or more adenomas a non-toxic therapeutically effective amount of compound of formula II

II or a pharmaceutically acceptable salt thereof wherein:

X—Y—Z— is selected from the group consisting of:

(a) —CH$_2$CH$_2$CH$_2$—,
(b) —C(O)CH$_2$CH$_2$—,
(c) —CH$_2$CH$_2$C(O)—,
(d) —CR$^5$(R$^{5'}$)—O—C(O)—,
(e) —C(O)—O—CR$^5$(R$^{5'}$)—,
(f) —CH$_2$—NR$^3$—CH$_2$—,
(g) —CR$^5$(R$^{5'}$)—NR$^3$—C(O)—,
(h) —CR$^4$=CR$^{4'}$—S—,
(i) —S—CR$^4$=CR$^{4'}$—,
(j) —S—N=CH—,
(k) —CH=N—S—,
(l) —N=CR$^4$—O—,
(m) —O—CR4=N—
(n) —N=CR$^4$—NH—,
(o) —N=CR$^4$—S—, and
(p) —S—CR$^4$=N—,
(q) —C(O)—NR$^3$—CR$^5$(R$^{5'}$)—,
(r) —NR$^3$—CH=CH— provided R$^1$ is other than —S(O)$_2$Me,
(s) —CH=CH—NR$^3$— provided R$^1$ is other than —S(O)$_2$Me, when side b is a double bond, and sides a an c are single bonds; and X—Y—Z— is selected from the group consisting of:

(a) =CH—O—CH=, and
(b) =CH—NR$^3$—CH=,
(c) =N—S—CH=,
(d) =CH—S—N=,
(e) =N—O—CH=,
(f) =CH—O—N=,
(g) =N—S—N=,
(h) =N—O—N=, when sides a and c are double bonds and side b is a single bond;

R$^1$ is selected from the group consisting of
(a) S(O)$_2$CH$_3$,
(b) S(O)$_2$NH$_2$,
(c) S(O)$_2$NHC(O)CF$_3$,
(d) S(O)(NH)CH$_3$,
(e) S(O)(NH)NH$_2$,
(f) S(O)(NH)NHC(O)CF$_3$,
(g) P(O)(CH$_3$)OH, and
(h) P(O)(CH$_3$)NH$_2$, R$^2$ is selected from the group consisting of
(a) C$_{1-6}$alkyl,
(b) C$_3$, C$_4$, C$_5$, C$_6$, and C$_7$, cycloalkyl,
(c) mono-, di- or tri-substituted phenyl wherein the substituent is selected from the group consisting of
(1) hydrogen,
(2) halo,
(3) C$_{1-6}$alkoxy,
(4) C$_{1-6}$alkylthio,
(5) CN,
(6) CF$_3$,
(7) C$_{1-6}$alkyl,
(8) N$_3$,
(9) —CO$_2$H,
(10) —CO$_2$—C$_{1-4}$alkyl,
(11) —C(R$^5$)(R$^6$)—OH,
(12) —C(R$^5$)(R$^6$)—O—C$_{1-4}$alkyl, and
(13) —C$_{1-6}$alkyl—CO$_2$—R$^5$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of
(1) hydrogen,
(2) halo, including fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH,
(10) —$C(R^5)(R^6)$—O—$C_{1-4}$alkyl;

$R^3$ is selected from the group consisting of
(a) hydrogen,
(b) $CF_3$,
(c) CN,
(d) $C_{1-6}$alkyl,
(e) hydroxy$C_{1-6}$alkyl, and
(f) —C(O)—$C_{1-6}$alkyl,
(g) optionally substituted
  (1) —$C_{1-5}$ alkyl-Q,
  (2) —$C_{1-3}$alkyl-O—$C_{1-3}$alkyl-Q,
  (3) —$C_{1-3}$alkyl-S—$C_{1-3}$alkyl-Q,
  (4) —$C_{1-5}$ alkyl-O—Q, or
  (5) —$C_{1-5}$ alkyl-S—Q,
    wherein the substituent resides on the alkyl and the substituent is $C_{1-3}$alkyl;
(h) —Q

$R^4$ and $R^{4'}$ are each independently selected from the group consisting of
(a) hydrogen,
(b) $CF_3$,
(c) CN,
(d) $C_{1-6}$alkyl,
(e) —Q,
(f) —O—Q;
(g) —S—Q, and
(h) optionally substituted
  (1) —$C_{1-5}$ alkyl-Q,
  (2) —O—$C_{1-5}$ alkyl-Q,
  (3) —S—$C_{1-5}$ alkyl-Q,
  (4) —$C_{1-3}$alkyl-O—$C_{1-3}$alkyl-Q,
  (5) —$C_{1-3}$alkyl-S—$C_{1-3}$alkyl-Q,
  (6) —$C_{1-5}$ alkyl-O—Q,
  (7) —$C_{1-5}$ alkyl-S—Q,
    wherein the substituent resides on the alkyl and the substituent is $C_{1-3}$alkyl, and $R^5$, $R^{5'}$ and $R^6$, $R^7$ and $R^8$ are each independently selected from the group consisting of
(a) hydrogen,
(b) $C_{1-6}$alkyl,
  or $R^5$ and $R^6$ or $R^7$ and $R^8$ together with the carbon to which they are attached form a monocyclic saturated carbon ring of 3, 4, 5, 6 or 7 atoms;

Q is $CO_2H$, $CO_2$—$C_{1-4}$alkyl, tetrazolyl-5-yl, $C(R^7)(R^8)$(OH), or $C(R^7)(R^8)$(O $C_{1-4}$alkyl);

provided that when X—Y—Z is —S—$CR^4$=$CR^{4'}$, then $R^4$ and $R^{4'}$ are other than $CF_3$.

Within this genus is a sub-genus directed to the use of compound of formula III or a pharmaceutically acceptable salt thereof wherein:
$R^1$ is selected from the group consisting of
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$, $R^2$ is selected from the group consisting of
(a) $C_{1-6}$alkyl,
(b) $C_3$, $C_4$, $C_5$, $C_6$, and $C_7$, cycloalkyl,
(c) mono-, di- or tri-substituted phenyl wherein the substituent is selected from the group consisting of
  (1) hydrogen,
  (2) halo,
  (3) $C_{1-6}$alkoxy,
  (4) $C_{1-6}$alkylthio,
  (5) CN,
  (6) $CF_3$,
  (7) $C_{1-6}$alkyl,
  (8) $N_3$,
  (9) —$CO_2H$,
  (10) —$CO_2$—$C_{1-4}$alkyl,
  (11) —$C(H)(R^6)$—OH,
  (12) —$C(H)(R^6)$—O—$C_{1-4}$alkyl, and
  (13) —$C_{1-6}$alkyl-$CO_2H$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of
  (1) hydrogen,
  (2) halo, including fluoro, chloro, bromo and iodo,
  (3) $C_{1-6}$alkyl,
  (4) $C_{1-6}$alkoxy,
  (5) $C_{1-6}$alkylthio,
  (6) CN,
  (7) $CF_3$,
  (8) $N_3$,
  (9) —$C(H)(R^6)$—OH,
  (10) —$C(H)(R^6)$—O—$C_{1-4}$alkyl;

$R^5$ and $R^{5'}$ are each methyl or ethyl, or
$R^5$ and $R^{5'}$ are each hydrogen,
$R^6$ is selected from the group consisting of
(a) hydrogen,
(b) $C_{1-6}$alkyl.

Within this sub-genus is a class directed to the use of compound of formula III wherein $R^1$ is selected from the group consisting of
- (a), $S(O)_2CH_3$,
- (b) $S(O)_2NH_2$,
- (c) $S(O)_2NHC(O)CF_3$,
- (d) $S(O)NHCH_3$,
- (e) $S(O)NHNH_2$, and
- (f) $S(O)NHNHC(O)CF_3$;

$R^2$ is selected from the group consisting of
- (a) $C_{1-4}$alkyl,
- (b) $C_3$, $C_4$, $C_5$, $C_6$, and $C_7$, cycloalkyl,
- (c) mono- or di-substituted phenyl wherein the substituent is selected from the group consisting of
  - (1) hydrogen,
  - (2) fluoro, chloro, and bromo,
  - (3) $C_{1-4}$alkoxy,
  - (4) $C_{1-4}$alkylthio,
  - (5) CN,
  - (6) $CF_3$,
  - (7) $C_{1-4}$alkyl,
  - (8) $N_3$,
  - (9) —$CO_2H$,
  - (10) —$CO_2$—$C_{1-3}$alkyl,
  - (11) —$C(H)(R^6)$—OH, and
  - (12) —$C(H)(R^6)$—O—$C_{1-3}$alkyl.

Within this class is a sub-class directed to the use of compound of formula III wherein
$R^2$ is selected from the group consisting of
- (a) cyclohexyl, and
- (b) mono- or di-substituted phenyl, and
  wherein the substitutents are selected from the group consisting of
  - (1) hydrogen,
  - (2) halo,
  - (3) $C_{1-4}$alkoxy,
  - (4) $C_{1-4}$alkylthio,
  - (5) CN,
  - (6) $CF_3$,
  - (7) $C_{1-4}$alkyl,
  - (8) $N_3$, and
  - (9) —$C(H)(R^6)$—OH;

Within this sub-class is a group directed to the use of compound of formula III wherein
$R^1$ is selected from the group consisting of
- (a) $S(O)_2CH_3$,
- (b) $S(O)_2NH_2$,
- (c) $S(O)NHCH_3$, and
- (d) $S(O)NHNH_2$;

$R^2$ is selected from the group consisting of
mono or di-substituted phenyl wherein the substitutents are selected from the group consisting of
- (1) hydrogen,
- (2) halo, selected from the group consisting of fluoro, chloro and bromo,
- (3) $C_{1-3}$alkoxy,
- (4) $C_{1-3}$alkylthio,
- (5) CN, and
- (6) $C_{1-3}$alkyl.

Illustrating the invention is the use of compounds selected from
- (1) 3-(3-Fluorophenyl)-4-(4-(methylsulfonyl)phenyl)-2-(5H)-furanone,
- (2) 3-(3,4-Difluorophenyl)-4-(4-(methylsulfonyl)phenyl)-2-(5H)-furanone,
- (3) 3-(3,4-Dichlorophenyl)-4-(4-(methylsulfonyl)phenyl)-2-(5H)-furanone,
- (4) 3-phenyl-4-(4-(methylsulfonyl)phenyl)-2-(5H)-furanone, and
- (5) 5,5-Dimethyl-3-(3-fluorophenyl)-4-(methylsulfonyl)phenyl)-2-(5H)-furanone or a pharmaceutically acceptable salt thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The $IC_{50}$ values represent the concentration of inhibitor required to return PGEsynthesis to 50 % of that obtained as compared to the uninhibited control.

For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg. Once a day dosage is anticipated.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The examples below are intended to illustrate, but not limit the invention as disclosed herein.

EXAMPLES

Patient Samples

Colon cancer and matched normal mucosal tissues, adenomatous polyps, normal colonic mucosa from non-cancer patients and matched normal and cancerous breast tissues were examined. The mean age and range of matched normal and colon cancer samples were 63.3 and 41–93 years, respectively. Colon tissue specimens were obtained from a non-necrotic area of the tumor and from autologous normal mucosa from the same patient at a resection margin located at more than 5 cm from the tumor. Histologically, all colon tumors were adenocarcinomas and all patients had sporadic colon cancer. One patient had a focus of adeno-carcinoma within an adenomatous polyp. Colonic adenomas were from patients with familial adenomatous polyposis (FAP).

Preparation of Microsomal Membranes from Colon Tissues

Frozen tissues were thawed in ice-cold homogenization buffer [50 mM potassium phosphate, pH 7.1, containing 0.1 M NaCl, 2 mM EDTA, 0.4 mM phenylmethylsulfonyl fluoride, 60 µg/ml soybean trypsin inhibitor, 2 µg/ml leupeptin, 2 µg/ml aprotinin and 2 µg/ml pepstatin, all from Sigma Chemical Co., St. Louis, Mo.). Tissues were disrupted twice on ice using a tissue tearer (Biospec Products, Bartlesville, Okla.) and homogenized by sonication at 4° C. using a Cole Parmer 4710 series ultrasonic homogenizer (Cole Parmer Instrument Co., Chicago, Ill.). Cellular debris was removed by centrifugation at 1,000×g for 15 min at 4° C. and the resultant supernatants were subjected to centrifugation at 100,000×g for 60 min at 4° C. Membrane fractions were resuspended in homogenization buffer and sonicated in order to obtain a homogenous membrane suspension. Protein concentrations were determined for each sample using a protein assay kit (Bio-Rad, Mississauga, Ontario, Canada).

Antisera

Full-length sheep seminal vesicle PGHS-1 and placental PGHS-2 purified proteins were purchased from Cayman (Ann Arbor, Mich.) and used to generate rabbit polyclonal antibodies. New Zealand White female rabbits were injected with 1 ml of Freund's complete adjuvant containing 200 µg of purified PGHS-1 or PGHS-2. Two weeks after the primary injection, rabbits were boosted with 100 µg of purified PGHS-1 or PGHS-2 in 0.5 ml of Freund's incomplete adjuvant. The anti-PGHS antisera recognize the homologous human PGHS isoforms with approximately one thousand-fold selectivity for the appropriate isoform. Under the conditions used in this study, the anti-PGHS antibodies demonstrated no significant cross-reactivity with the alternate PGHS isoform. For each experiment, two concentrations of both PGHS-1 and PGHS-2 proteins standards were loaded on each gel to assess selectivity of the antibodies.

Sodium Dodecyl Sulfate Polyacrylamide Gel Electrophoresis (SDS-PAGE) and Immunoblot Analysis Membrane fractions were mixed with sodium dodecyl sulfate (SDS) sample buffer (20 mM Tris-HCl, pH 6.8, containing 0.4% (w/v) SDS, 4% glycerol, 0.24 M β-mercaptoethanol, and 0.5% bromphenol blue), boiled for 5 min and analyzed by SDS-polyacrylamide gel electrophoresis according to the method of Laemmli (Laemmli, U. K. Cleavage of structural proteins during the assembly of the head of bacteriophage T4. Nature, 227; 680–685, 1970). Proteins were electrophoretically transferred to nitrocellulose membranes as described previously (Towbin, H., Staehelin, T. and Gordon, J. Electrophoretic transfer of proteins from polyacrylamide gels to nitrocellulose sheets: procedure and some applications. Proc. Natl. Acad. Sci. USA, 75; 4350–4354, 1979). Primary antibodies to PGHS-1 and PGHS-2 were used at a final dilution of 1:5,000 and 1:7,500, respectively. The secondary horse radish peroxidase-linked donkey anti-rabbit IgG antibody (Amersham Life Sciences, Oakville, Ontario, Canada) was used at a dilution of 1:3,000. Immunodetection was performed using enhanced chemiluminescence according to the manufacturer's instructions (Amersham). Autoradiographs were scanned using a computing densitometer (Molecular Dynamics, Sunnyvale, Calif.) and the volume of optical density corresponding to the purified PGHS isoform was used to calculate quantity (ng) of PGHS protein in histologically normal colonic and tumor tissue.

Statistical Analysis

The results of this study were analyzed by a Wilcoxon signed-rank non-parametric test to determine significant differences between normal and tumor PGHS-1 and PGHS-2 levels (Freund, J. E. Mathematical Statistics. Prentice Hall, Englewood Cliffs, N.J. 1992).

Results

Expression of PGHS-1 in Human Colon: Normal and Tumor Tissue

FIG. 1 is a representative immunoblot demonstrating PGHS expression in 4 of the 25 patients examined in this study. The 72 kD band, which is the reported molecular weight for PGHS-1 (Otto, J. C., DeWitt, D. L. S., and Smith, W. L. N-glycosylation of prostaglandin endoperoxide synthases-1 and -2 and their orientations in the endoplasmic reticulum. J. Biol.Chem., 268; 18234–18242, 1993), comigrated with purified sheep seminal vesicle PGHS-1 standard (FIG. 1A) and with recombinant human PGHS-1 expressed in COS-7 cells (data not shown; 7). The immunoblot results from all 25 patients were quantitated by densitometric analysis and are shown in the bar graph in FIG. 2. In 21 of 25 patient, PGHS-1 levels were reduced in tumor tissue as compared to normal colon. The mean decrease of PGHS-1 in tumor as compared to normal tissue for all 25 patients examined was 170 ng per mg microsomal protein. In comparison to the purified PGHS-1 standard, the range of concentrations of PGHS-1 in normal and tumor tissue were 0–760 ng (median, 199.8) and 4–540 ng (median, 51.1) per mg microsomal protein, respectively. The difference in PGHS-1 expression in normal versus tumor tissue was highly statistically significant as determined by nonparametric analyses (Wilcoxon signed-rank test, $p<0.0001$).

Expression of PGHS-2 in Human Colon: Normal and Tumor Tissue

A representative immunoblot analysis of 4 of the 25 matched colon samples using a specific anti-PGHS-2 antibody is shown in FIG. 1B. Duplicate immunoblots were performed in order to assess the expression of PGHS-1 (FIG. 1A) and PGHS-2 (FIG. 1B) in samples derived from the same patient. PGHS-2 immunoreactivity was not detected in any of the 4 normal colon tissue samples. In contrast, immunoreactive bands of 70–72 kD, which comigrated with purified sheep placental PGHS-2 (FIG. 1B) and human recombinant PGHS-2 expressed in COS-7 cells (data not shown; 7), were detected in tumor tissue of 3 of the 4 patients shown here. In total, PGHS-2 immunoreactive protein was detected in tumor tissue from 19 out of 25 patients examined (FIG. 2). Overall, the mean PGHS-2 increase in colonic tumors for all 25 patients examined was approximately 73 ng per mg microsomal protein. In comparison to the PGHS-2 standard, the range of concentrations of PGHS-2 immunoreactive protein in normal and tumor tissue was 0–49 ng (median, 3.8 ng) and 1.6–580 ng (median, 37.7 ng), per mg microsomal protein, respectively. The difference in PGHS-2 expression in normal versus tumor tissue was highly statistically significant as determined by nonparametric analyses (Wilcoxon signed-rank test, p<0.0001).

Colonic tumors are classified by 4 Dukes' stages: A, tumor within the intestinal mucosa; B, tumor into muscularis mucosa; C, metastasis to lymph nodes and D, metastasis to other tissues. In this study, colonic tumors were from patients with all stages of Dukes' classification (Table 1).

The expression of PGHS-1 and -2 protein was analyzed in a variety of other human tissues including 5 colon tissues from non-cancer patients, 4 premalignant polyps and 3 matched normal and cancerous breast tissues. Although PGHS-1 protein was observed in normal and cancer tissues, PGHS-2 protein was not detected in any of these samples.

Discussion

In this study, 19 out of 25 colon tumors examined expressed PGHS-2 protein whereas only 2 out of 25 normal

TABLE 1

Patient Data

| Patient # | Medication | Dukes Stage | Change in Protein Expression (ng) | |
|---|---|---|---|---|
| | | | PGHS-2 | PGHS-1 |
| 1 | NA | NA | 6.20 | −10.00 |
| 2 | NA | NA | 1.70 | −6.00 |
| 3 | NA | NA | 2.80 | −9.40 |
| 4 | NA | NA | 1.20 | −4.10 |
| 5 | NONE | B | 0.10 | ND |
| 6 | chlordiazepoxide hydrochloride/clidinium bromide, magaldrate | C | 3.20 | −5.90 |
| 7 | NSAID | A | 0.00 | −17.30 |
| 8 | levothyroxine sodium, Iorazepam, omeprazole | C | 0.50 | 1.50 |
| 9 | NONE | C | 0.90 | 0.50 |
| 10 | NA | C | 4.70 | −16.30 |
| 11 | NONE | B | 0.90 | −9.00 |
| 12 | NA | D | −0.20 | −14.40 |
| 13 | NA | B | 4.30 | −7.10 |
| 14 | aspirin | C | 0.80 | −5.60 |
| 15 | deltacortisone, azathioprine, Iovastatin | B | 0.00 | 5.70 |
| 16 | enalapril maleate | B | 25.60 | −6.60 |
| 17 | NONE | B | −0.30 | −1.50 |
| 18 | NONE | B | 9.70 | −11.20 |
| 19 | aspirin | C | 13.70 | −11.10 |
| 20 | NONE | B | 8.30 | −5.90 |
| 21 | NONE | C | −0.10 | −9.30 |
| 22 | aspirin | C | 0.20 | −3.00 |
| 23 | none | C | 0.00 | −12.30 |
| 24 | diltiazem hydrochloride, omeprazole | B | 2.20 | −17.00 |
| 25 | flurbiprofen, aspirin, nifedipine, metoprolol tartrate | B | 0.10 | −10.00 |

NA = data not available
ND = not detectable
Dukes Stages:
A = tumor within mucosa
B = tumor into muscularis mucosa
C = metastasis to lymph nodes
D = metastasis to other tissues Table 1. Patient data. Information for each patient examined in this study is shown. When available, medications taken by patients are indicated. Dukes stage of disease is as follows: A=tumor within mucosa; B=tumor into muscularis mucosa; C=metastasis to lymph nodes and D=metastasis to other tissues. Amount of PGHS immunoreactive protein is expressed as relative change in expression from normal colonic mucosa to tumor tissue. NA: data not available and ND: immunoreactivity not detectable.

There was no association between stage and change in expression of PGHS-1 or PGHS-2 protein. This lack of association is consistent with the observation that $PGE_2$ levels in human colon tumors do not appear to correlate with Dukes' stage (Rigas, B., Goldman, I. S., and Levine, L. Altered eicosanoid levels in human colon cancer. J. Lab. Clin. Med., 122; 518–523, 1993). Interestingly, PGHS-2 expression was either low or undetectable in 5 out of 6 patients currently using anti-inflammatory medications (Table 1).

Expression of PGHS-1 and -2 Protein in Normal Colon, Premalignant Polyps and Matched Normal and Breast Cancer Tissue colon tissue samples expressed this protein. Concomitant with the induced expression of PGHS-2, PGHS-1 expression was reduced in 21 out of 25 of the tumor samples in comparison with normal adjacent colonic mucosa; however, PGHS-1 protein concentrations were similar in control colon and polyp samples.

To our knowledge, this is the first study examining the expression of PGHS-1 and -2 protein in human colon cancer. Previous research has shown increased eicosanoid levels, in particular, $PGE_2$, in human colon cancer (Rigas, B., Goldman, I. S., and Levine, L. Altered eicosanoid levels in human colon cancer. J. Lab. Clin. Med., 122; 518–523, 1993, Bennett, A., Del Tacca, M., Stamford, I. F., and Zebro, T. Prostaglandins from tumours of human large bowel. Br. J. Cancer, 35; 881–884, 1977, Bennett, A., Civier, A., Hensby, C. N., Melhuish, P. B., and Stamford, I. F. Measurement of arachidonate and its metabolites extracted from human normal and malignant gastrointestinal tissues. Gut, 28; 315–318, 1987). We conclude the increase in PGHS-2 enzyme that we observe in colonic tumor tissue results in elevated prostaglandin levels in these tumors. Moreover, we conclude that since prostaglandins may have multiple effects in the biology of cancer, including growth promotion and modulation of immune surveillance, elevated prostanoid levels within tumors will aid in tumor growth or development (Earnest, D. L., Hixson, L. J., and Alberts, D. S. Piroxicam and other cyclooxygenase inhibitors: potential for cancer chemoprevention. J. Cell. Biochem., 161 (Suppl.); 156–166, 1992). Interestingly, PGHS-2 protein was not observed in the examination of breast cancer samples. Thus, PGHS-2 protein expression is a typical feature in the transformation of tissue from pro-malignant to malignant phases.

Eberhart and his coworkers demonstrated up-regulation of PGHS-2 mRNA in human colorectal adenomas and adenocarcinomas (Eberhart, C. E., Coffey, R. J., Radhika, A., Giardiello, F. M., Ferrenbach, S., Dubois, R. N. Up-regulation of cyclooxygenase 2 gene expression in human colorectal adenomas and adenocarcinomas. Gastroenterology, 107; 1183–1188, 1994). While this is an interesting finding, this finding but may not be indicative of actual enzyme expression due to the complex post-transcriptional and -translational regulation of PGHS-2 mRNA. For example, Hoff et al. (Hoff, T., DeWitt, D., Kaever, V., Resch, K. and Goppelt-Struebe, M. Differentiation-associated expression of prostaglandin G/H synthase in monocytic cells. FEBS Lett., 320; 38–42, 1993), Lee et al (Lee, S. H., Soyoola, E., Chanmugam, P., Hart, S., Sun, W., Zhong, H., Liou, S., Simmons, D., and Hwang, D. Selective expression of mitogen-inducible cyclooxygenase in macrophages stimulated with lipopolysaccharide. J. Biol. Chem., 267; 25934–25938, 1992) and our laboratories have shown substantial expression of PGHS-2 mRNA without concomitant expression of PGHS-2 protein. Therefore, examination of PGHS protein expression is critical to estimate the concentration of PGHS-2 enzyme.

Nothing in the art would suggest the absence of PGHS-2 protein in polyps from 4 patients with familial adenomatous polyposis, especially in light of evidence by several groups that sulindac (inhibiting both PGHS-1 and PGHS-2) results in polyp regression in patients with familial polyposis. The human polyp samples were pools of small colon polyps ranging in size from 0.4–<5 mm in diameter. In our opinion, PGHS-2 protein is expressed at a later stage in the polyp-cancer sequence, when polyps are larger in diameter, perhaps greater than or equal to 5 mm in size. A recent study by Ladenheim et. al. reports that sulindac did not result in a regression of sporadic colonic polyps; however, they emphasized that their study addressed early sporadic polyps (67% of the polyps were <5 mm) and suggested that response to NSAIDs may be more favorable in polyps at a "particular stage along the adenoma-carcinoma sequence (Ladenheim, J., Garcia, G., Titzer, D., Herzenberg, H., Lavori, P., Edson, R., and Omary, B. Effect of sulindac on sporadic colonic polyps. Gastroenterology, 108; 1083–1087, 1995)."

The prolonged use of NSAIDs is associated with side effects including renal toxicity, gastrointestinal ulceration and increased bleeding. Current NSAIDs such as aspirin, sulindac and indomethacin, have little selectivity for inhibition of either PGHS-1 or PGHS-2 (Battistini, B., Botting, R., and Bakhle, Y. S. COX-1 and COX-2: Toward the development of more selective NSAIDS. Drug News Perspectives, 7; 501–512, 1994, O'Neill, G. P., Mancini, J. A., Kargman, S., Yergey, J., Kwan, M. Y., Falgueyret, J.-P., Abramovitz, M., Kennedy, B. P., Ouellet, M., Cromlish, W., Culp, S., Evans, J. F., Ford-Hutchinson, A. W. and Vickers, P. J. Overexpression of human prostaglandin G/H synthase-1 and -2 by recombinant vaccinia virus: inhibition by nonsteroidal anti-inflammatory drugs and biosynthesis of 15-hydroxyeicosatetraenoic acid. Mol. Pharmacol., 45; 245–254, 1994, DeWitt, D. L., Meade, E. A., and Smith, W. L. PGH synthase isoenzyme selectivity: the potential for safer nonsteroidal antiinflammatory drugs. Am. J. Med. (Suppl.), 95; 40S–44S, 1993). It has been suggested that selective inhibitors of PGHS-2 would have useful therapeutic effect with a decreased capacity to induce mechanism-based side effects. Recently, a selective PGHS-2 inhibitor, NS-398, has been shown in the rat to have antiinflammatory, antipyretic and analgesic effects without being ulcerogenic (Futaki, N., Yoshikawa, K., Hamasaka, Y., Arai, I., Higuchi, S., Iizuka, H., and Otomo, S. NS-398, a novel non-steroidal anti-inflammatory drug with potent analgesic and antipyretic effects, which causes minimal stomach lesions. Gen. Pharmacol., 24; 105–110, 1993; Futaki, N., Takahashi, S., Yokoyama, M., Arai, I., Higuchi, S. and Otomo, S. NS-398, a new anti-inflammatory agent, selectively inhibits prostaglandin G/H synthase/cyclooxygenase (COX-2) activity in vitro. Prostaglandins, 47; 55–59, 1994). The present study examining the expression of PGHS-1 and PGHS-2 in the colon demonstrates that both PGHS isoforms are present in colon tumors.

Mouse Polyps

ApcΔ716 knockout mice (developed by Dr. Taketo at Banyu Merck, ref: Oshima, M., Oshima, H., Kitagawa, K., Kobayashi, M., Itakura, C. and Taketo, M. Loss of Apc heterozygosity and abnormal tissue building in nascent intestinal polyps in mice carrying a truncated Apc genetruncation mutant mice. Proc. Natl. Acad. Sci. USA, 92, 4482–4486, 1995) develop multiple polyps throughout their intestinal tracts. Small intestinal and colonic polyp samples ranging in size from 0.3–5.6 mm from ApcΔ716 knockout mice were collected and immediately frozen from six mice (both males and females) from backcross N1, N2 and N4 generation mice.

RESULTS

Expression of PGHS-1 and PGHS-2 in ApcΔ716 Mouse Polyps

PGHS-1 and PGHS-2 protein expression was examined in polyps of increasing size from ApcΔ716 mice. FIG. 3 is an immunoblot analyses demonstrating PGHS-1 and PGHS-2 expression in polyps ranging in size from 0.3–5 mm in diameter. (Lanes 1–5 correspond to samples derived from polyps of approximately 1–5 mm in diameter, respectively.) PGHS-1 protein was demonstrated in all intestinal and colonic control and polyps samples. PGHS-2 immunoreactivity was not detected in control intestine or colon samples. Although low levels of PGHS-2 protein were detected in larger intestinal polyps (3–5 mm in diameter) (lanes 3,4 and 5), higher levels of PGHS-2 immunoreactive species were detected in all colonic polyp samples ranging in size from 1–5 mm in diameter (lanes 1–5) with very high levels of PGHS-2 protein being demonstrated in polyps of 2–3 mm in diameter (lanes 2 and 3). Purified sheep PGHS-1 and PGHS-2 protein (5 ng, 10 ng, and 20 ng) were electrophoresed as standards and are labeled accordingly. We believe that the dramatic induction of COX-2 during polyp growth reflects a critical roll for COX-2 in the initiation of the transformation from ademona to adenocarcinoma.

What is claimed is:

1. A method of treating colonic adenomas in a patient in need thereof comprising administering to said patient a non-toxic therapeutically effective amount of an NSAID, with the proviso that said NSAID is not aspirin, ibuprofen, indomethacin, sulindac, dolobid, diclofenac, naproxen, piroxicam, etodolac, ketoprofen, flurbiprofen, meloxicam, flosulide or nabumetone, wherein said NSAID is a potent inhibitor of PGHS-2 and wherein said NSAID possesses a selectivity for inhibiting PGHS-2 over PGHS-1 of at least 100 fold as measured by the ratio of the $IC_{50}$ for the inhibition of PGHS-2 to the $IC_{50}$ for the inhibition of PGHS-1 in a whole cell or microsomal assay, said assay conducted by measuring the amount of prostaglandin $E_2$ synthesized in the presence of arachidonic acid, PGHS-2 or PGHS-1 enzyme and said NSAID, and wherein said assay comprises the steps of:

(1) incubating said NSAID with the cell or microsome expressing PGHS-2 or PGHS-1 enzyme for about 10 to 20 minutes prior to the addition of arachidonic acid, and (2) conducting said assay with arachidonic acid at a concentration of about 10 $\mu$M.

2. The method of treating colonic adenomas in accordance with claim 1 wherein the patient has a history of FAP.

3. The method of treating colonic adenomas in accordance with claim 1 wherein the patient has one or more of said adenomas.

4. The method of treating colonic adenomas according to claim 1, wherein the NSAID is administered at a dose of about 0.5 mg to about 7 g per patient per day.

5. The method of treating colonic adenomas in accordance with claim 1 wherein said NSAID possesses a potency for the inhibition of PGHS-2 of about 1 $\mu$M or less as measured by the $IC_{50}$ for the inhibition of PGHS-2 in a whole cell or microsomal assay.

6. The method of treating colonic adenomas in accordance with claim 5 wherein the selectivity and potency of said NSAID are measured in a whole cell assay.

7. The method of treating or preventing colonic adenomas in accordance with claim 6 wherein the cells used for the whole cell assay are the human osteosarcoma 143 cells for cyclooxygenase-2 and the human U-937 cells for cyclooxygenase-1.

8. The method of treating colonic adenomas in accordance with claim 5 wherein the selectivity and potency of said NSAID are measured in a microsomal assay.

9. The method of treating colonic adenomas in accordance with claim 8 wherein the cells from which the microsomes were prepared are the human osteosarcoma 143 cells for PGHS-2 and the human U-937 cells for PGHS-1.

10. A method of treating colonic adenomas in a patient in need thereof comprising administering to said patient a non-toxic therapeutically effective amount of an NSAID, with the proviso that said NSAID is not aspirin, ibuprofen, indomethacin, sulindac, dolobid, diclofenac, naproxen, piroxicam, etodolac, ketoprofen, flurbiprofen, meloxicam, flosulide or nabumetone, wherein said NSAID is a potent inhibitor of PGHS-2 and wherein said NSAID possesses a selectivity for inhibiting PGHS-2 over PGHS-1 of at least 100 fold as measured by the ratio of $IC_{50}$ for the inhibition of PGHS-2 to the $IC_{50}$ for the inhibition of PGHS-1 in a microsomal assay, said assay conducted by measuring the amount of prostaglandin $E_2$ synthesized in the presence of arachidonic acid, PGHS-2 or PGHS-1 enzyme and said NSAID, and wherein said assay comprises the steps of:

(1) incubating said NSAID with the microsome expressing PGHS-2 or PGHS-1 enzyme for about 10 to 20 minutes prior to the addition of arachidonic acid, and (2) conducting said assay with arachidonic acid at a concentration of about 10 $\mu$M, wherein said NSAID possesses a potency for the inhibition of PGHS-2 of about 1 $\mu$M or less as measured by the $IC_{50}$ for the inhibition of PGHS-2 in the microsomal assay, and wherein the microsomal assay is the CHAPS-solubilized recombinant PGHS-1 or PGHS-2 expressing insect cell membrane assay.

11. A method of retarding or preventing the transformation of a colonic adenoma to a colonic adenocarcinoma in a patient in need thereof comprising administering to said patient a non-toxic therapeutically effective amount of an NSAID, with the proviso that said NSAID is not aspirin, ibuprofen, indomethacin, sulindac, dolobid, diclofenac, naproxen, piroxicam, etodolac, ketoprofen, flurbiprofen, meloxicam, flosulide or nabumetone, wherein said NSAID is a potent inhibitor of PGHS-2 and wherein said NSAID possesses a selectivity for inhibiting PGHS-2 over PGHS-1 of at least 100 fold as measured by the ratio of $IC_{50}$ for the inhibition of PGHS-2 to the $IC_{50}$ for the inhibition of PGHS-1 in a microsomal assay, said assay conducted by measuring the amount of prostaglandin $E_2$ synthesized in the presence of arachidonic acid, PGHS-2 or PGHS-1 enzyme and said NSAID, and wherein said assay comprises the steps of:

(1) incubating said NSAID with the microsome expressing PGHS-2 or PGHS-1 enzyme for about 10 to 20 minutes prior to the addition of arachidonic acid, and (2) conducting said assay with arachidonic acid at a concentration of about 10 $\mu$M, wherein said NSAID possesses a potency for the inhibition of PGHS-2 of about 1 $\mu$M or less as measured by the $IC_{50}$ or the inhibition of PGHS-2 in the microsomal assay, and wherein the microsomal assay is the CHAPS-solubilized recombinant PGHS-1 or PGHS-2 expressing insect cell membrane assay.

12. A method of retarding or preventing the appearance of the capacity of an adenoma to invade the basement membrane of the submucosal issue of the colon in a patient in need thereof comprising administering to said patient a non-toxic therapeutically effective amount of an NSAID, with the proviso that said NSAID is not, aspirin, ibuprofen, indomethacin, sulindac, dolobid, diclofenac, naproxen, piroxicam, etodolac, ketoprofen, flurbiprofen, meloxicam, flosulide or nabumetone, wherein said NSAID is a potent inhibitor of PGHS-2 and wherein said NSAID possesses a selectivity for inhibiting PGHS-2 over PGHS-1 of at least 100 fold as measured by the ratio of $IC_{50}$ for the inhibition of PGHS-2 to the $IC_{50}$ for the inhibition of PGHS-1 in a microsomal assay, said assay conducted by measuring the amount of prostaglandin $E_2$ synthesized in the presence of arachidonic acid, PGHS-2 or PGHS-1 enzyme and said NSAID, and wherein said assay comprises the steps of:

(1) incubating said NSAID with the microsome expressing PGHS-2 or PGHS-1 enzyme for about 10 to 20 minutes prior to the addition of arachidonic acid, and (2) conducting said assay with arachidonic acid at a concentration of about 10 $\mu$M, wherein said NSAID possesses a potency for the inhibition of PGHS-2 of about 1 $\mu$M or less as measured by the $IC_{50}$ for the inhibition of PGHS-2 in the microsomal assay, and wherein the microsomal assay is the CHAPS-solubilized recombinant PGHS-1 or PGHS-2 expressing insect cell membrane assay.

13. A method of preventing colonic adenomas in a patient need thereof comprising administering to said patient a non-toxic therapeutically effective amount of an NSAID, with the proviso that, said NSAID is not aspirin, ibuprofen, indomethacin, sulindac, dolobid, diclofenac, naproxen, piroxicam, etodolac, ketoprofen, flurbiprofen, meloxicam, flosulide or nabumetone, wherein said NSAID possesses a selectivity for inhibiting PGHS-2 over PGHS-1 of at least 100 fold as measured by the ratio of the $IC_{50}$ for the inhibition of PGHS-2 to the $IC_{50}$ for the inhibition of PGHS-1 in a whole cell or microsomal assay, said assay conducted by measuring the amount o prostaglandin $E_2$ synthesized in the presence of arachidonic acid, PGHS-2 or PGHS-1 enzyme and said NSAID, and wherein said assay comprises the steps of:

(1) incubating said NSAID with the cell or microsome expressing PGHS-2 or PGHS-1 enzyme for about 10 to 20 minutes prior to the addition of arachidonic acid, and (2) conducting said assay with arachidonic acid at a concentration of about 10 $\mu M$.

14. The method of preventing colonic adenomas in accordance with claim 13 wherein the patient has a history of FAP.

15. The method of preventing colonic adenomas in accordance with claim 13 wherein the patient has one or more of said adenomas.

16. The method of preventing colonic adenomas in accordance with claim 13 wherein said NSAID possesses a potency for the inhibition of PGHS-2 of about 1 $\mu M$ or less as measured by the $IC_{50}$ for the inhibition of PGHS-2 in a whole cell or microsomal assay.

17. The method of preventing colonic adenomas in accordance with claim 16 wherein the selectivity and potency of said NSAID are measured in a whole cell assay.

18. The method of preventing colonic adenomas in accordance with claim 16 wherein the selectivity and potency of said NSAID are measured in a microsomal assay.

19. The method of preventing colonic adenomas in accordance with claim 17 wherein the cells from which the microsomes were prepared are the human osteosarcoma 143 cells for PGHS-2 and the human U-937 cells for PGHS-1.

* * * * *